United States Patent [19]

Gardner et al.

[11] 4,208,478

[45] Jun. 17, 1980

[54] TELLURIUM(II) PHOTOGRAPHIC MATERIALS

[75] Inventors: Sylvia A. Gardner; Henry J. Gysling, both of Rochester, N.Y.

[73] Assignee: Eastman Kodak Company, Rochester, N.Y.

[21] Appl. No.: 841,857

[22] Filed: Oct. 13, 1977

[51] Int. Cl.$^2$ .......................... G03C 5/24; G03C 1/00; G03C 1/02

[52] U.S. Cl. .................................... 430/616; 430/348; 430/353; 430/617; 430/964

[58] Field of Search ................... 96/48 HD, 88, 114.1, 96/48 PD; 260/437 R, 429.7, 448.2 N, 429 R

[56] References Cited

U.S. PATENT DOCUMENTS 3,811,895  5/1974  Ehrlich .................................. 96/88

*Primary Examiner*—Edward C. Kimlin
*Attorney, Agent, or Firm*—Richard E. Knapp

[57] ABSTRACT

A Te(II) complex represented by the formula: RTeM(R')$_3$ wherein M is lead, tin, germanium or silicon; R and R' are alkyl or aryl is useful in an imaging material to provide a non-silver image. The imaging material can be a photographic material, especially a heat-developable photographic material containing, for example, a photosensitive metal salt other than the Te(II) material or other sources of developable nuclei.

43 Claims, No Drawings

TELLURIUM(II) PHOTOGRAPHIC MATERIALS

BACKGROUND OF THE INVENTION

1. Field of the Invention

This invention relates to imaging materials comprising certain Te(II) complexes containing both a tellurium atom and a Pb, Sn, Ge or Si atom. In one aspect it relates to a photographic material comprising the described Te(II) complexes, such as a photothermographic material containing a combination of (a) a photosensitive metal salt with (b) an image-forming combination containing the described Te(II) complex and other components.

In another aspect it relates to a process of developing an image in a heat-developable photographic material containing the described tellurium complex. A further aspect of the invention relates to a heat-developable imaging material containing certain physically developable nuclei and an oxidation-reduction image-forming combination containing the described Te(II) complex. Another aspect of the invention relates to certain novel Te(II) complexes containing a Pb, Sn, Ge or Si atom and processes of preparing the described complexes.

2. Description of the State of the Art

It is known to provide an image in an imaging material containing certain metal complexes, such as certain tellurium complexes. These materials can be useful in what are described as photographic materials for dry processing with heat. These imaging materials are sometimes described as heat developable photographic materials or photothermographic materials. Such heat developable photographic materials after imagewise exposure to provide a developable latent image are heated to provide a developed image in the absence of processing solutions or baths.

It has been desirable to provide reduced silver concentrations in photosensitive silver materials, especially heat developable silver imaging materials. Attempts have been made in the past to provide this desired reduced silver concentration. For example, U.S. Pat. No. 3,152,903 of Shepard et al, issued Oct. 13, 1964 describes an imaging material containing a non-silver component such as titanium dioxide or zinc oxide. It is indicated that the image-forming composition can comprise a latent irreversible oxidation-reduction reaction combination which is capable of initiation by electron transfer from a non-silver photocatalyst. The photocatalyst can be, for example, zinc oxide or titanium dioxide. A disadvantage of the imaging material described in this patent is that no image amplification is possible. This provides the necessary requirement of undesirably high concentrations of non-silver materials. It has been desirable to overcome this problem by providing a more effective non-silver heat developable material, that is a material which enables desired latent image amplification.

An image amplification step is an important factor in photographic materials having increased speed. In increased speed materials, a latent image is generally formed by imagewise exposure of the photosensitive material to suitable radiation. The resulting invisible or latent image formed is then used to catalyze the reduction of a material in a high oxidation state to a visible image in a low oxidation state. In silver halide photographic materials, for example, exposure of photographic silver halide to light results in formation of silver nuclei which then can catalyze the further reduction of silver halide to silver in the presence of a reducing agent.

The use of tellurium materials in imaging is known. For instance, it is known to produce tellurium imaging by disproportionation of tellurium dihalides. Imaging materials are known in which images are formed by disproportionation of certain metal compounds such as tellrium halides. The images are formed in the presence of a processing liquid or solution which aids in the disproportionation reaction. The unexposed dihalides, however, are dark in color causing poor image discrimination. The tellurium dihalides are typically unstable in air and undergo light induced decomposition only when moistened with an organic solvent. This is a disadvantage in most imaging materials, especially those designed for processing in the absence of solutions or baths.

Other tellurium imaging materials include those which are certain Te(IV) compounds wherein the tellurium is bonded directly to a carbon atom. These tellurium materials undergo what can be described as a unit quantum photoreduction to yield a tellurium image. The materials and imaging process do not involve a catalytic amplification of a latent image. That is, the tellurium (O) formed upon exposure does not catalyze the decomposition of other components or other reaction of the Te(IV) compounds. The process and imaging material are inherently photographically slow in speed and limited in usefulness because they do not enable an amplification reaction.

An imaging combination comprising (1) a tellurium complex as an oxidizing agent with (2) a reducing agent is known to provide an amplified image in certain imaging combinations is described in U.S. Application Ser. No. 703,477 of Lelental and Gysling, filed July 8, 1976, now abandoned and related to U.S. 4,144,062 and U.S. 4,152,155. This imaging combination can be useful in heat developable photographic materials containing, for example, photographic silver halide or other sources of developable nuclei. The tellurium complexes, however, do not involve metallic atoms other than tellurium atoms. It has been found that the inclusion of other metal atoms in the tellurium complex provides an added source of imaging metal.

Tellurium compounds and complexes have been proposed for other purposes including other imaging materials. While these materials include tellurium compounds and complexes, none involve the formation of an image with a tellurium complex containing other than a tellurium atom as a source of metal for imaging.

Tellurium complexes are known which contain not only a tellurium atom but also an atom of some other metal, such as Si, Ge, Sn or Pb. These are described, for instance, in the following publications: (1) "The Organic Chemistry of Tellurium", by Kurt J. Irgolic, Gordon N. Breach Science Publishers, 1974, such as on pages 247–254; and (2) Zhurnal Obschchei Khimii, Volume 37, No. 5, pages 1037–1040, May, 1967. The latter publication describes, for instance, the tellurium compounds or complexes: (a) $(C_2H_5)_3MTeC_2H_5$ and (b) $(C_2H_5)_3MTeSn(C_2H_5)_3$ wherein M is Si or Ge. Also, none describe a process which enables the formation of the described tellurium materials that eliminates the need for a multistep process and the need for purification before using the tellurium compound or complex in an imaging material, such as a photothermographic material.

Materials are known in the imaging art in which metal nuclei are used for physical development purposes. None of these materials, however, involve nuclei in a heat developable photosensitive material containing a tellurium compound or complex which contains, in addition to the tellurium atom, an atom of, for example, germanium, tin, lead or silicon.

There has been a continuing need to provide improved tellurium imaging materials and processes. This continuing need has been especially true for heat developable photosensitive materials which enable amplification of a nuclei image. There has also been a need to provide improved tellurium complexes which contain the described non-tellurium metal atoms and to provide improved processes which eliminate the need for preparing the described tellurium complexes in multiple steps.

SUMMARY OF THE INVENTION

It has been found according to the invention that an image can be provided in a photographic material comprising a photographic Te(II) complex represented by the formula:

$$RTeM(R')_3$$

wherein M is lead, tin, germanium or silicon; R and R' are independently selected from the group consisting of alkyl containing 1 to 12 carbon atoms and aryl containing 6 to 12 carbon atoms. The described tellurium complex containing a Pb, Sn, Ge or Si atom has been found especially useful in a photothermographic material comprising, in reactive association, (a) a photosensitive metal salt, as described herein, with (b) an image-forming combination comprising (i) the described Te(II) complex with (ii) a reducing agent.

The described tellurium complexes according to the invention have been found to provide a useful image in, for example, a photothermographic material comprising, in reactive association, (a) a photosensitive metal compound selected from the group consisting of photosensitive silver, copper, tellurium and palladium compounds, and combinations thereof, with (b) an image-forming combination comprising (i) the described Te(II) complex with (ii) a reducing agent.

It has further been found that an imaging material according to the invention can comprise, in reactive association, (a) physically developable metal nuclei selected from the group consisting of chromium, iron, cobalt, nickel, copper, cadmium, selenium, palladium, silver, tin, tellurium, osmium, iridium, rhenium, ruthenium, platinum, gold and lead nuclei, and combinations of these nuclei, with (b) an image-forming combination comprising (i) the described Te(II) complex and (ii) a reducing agent.

A latent image in the described photosensitive material containing the described Te(II) complex can be developed, such as by heat development. For example, the latent image formed can be developed by merely heating the material to moderately elevated temperatures to provide a developed image, in the absence of processing solutions or baths.

An advantage of the described imaging materials, especially the described heat developable photosensitive materials, is that they enable an amplification factor which is significantly higher than expected compared to other prior art organo tellurium compounds.

It has also been found according to the invention that certain of the described Te(II) complexes are new complexes. These include complexes represented by the formula: RTeM(R')$_3$ wherein M is lead, tin, germanium or silicon; R and R' are each aryl containing 6 to 12 carbon atoms, such as phenyl. These new Te(II) complexes and complexes of Te(II) as described wherein R and R' are alkyl can be prepared, according to the invention by a simplified method that eliminates the need for synthesis of these complexes in several steps. This simplified method comprises preparing a Te(II) complex, as described, wherein R and R' are individually alkyl or aryl, by (a) reacting a diaryl or dialkyl ditelluride containing up to 12 carbon atoms with a reducing agent and an alkali metal hydroxide to provide an alkali metal salt of said telluride, and then (b) reacting the resulting alkali metal salt from (a) with a compound represented by the formula: M(R')$_3$Cl to provide said Te(II) complex. This method can be carried out without separating the described product from (a).

DETAILED DESCRIPTION OF THE INVENTION

One important embodiment of the invention is a photographic element comprising a support having thereon a photographic Te(II) complex represented by the formula: RTeM(R')$_3$ wherein M is lead, tin, germanium or silicon; R and R' are independently selected from the group consisting of alkyl containing 1 to 12 carbon atoms, such as methyl, ethyl, propyl, butyl, pentyl, hexyl and benzyl, and aryl containing 6 to 12 carbon atoms, such as phenyl, tolyl, anisyl, bromophenyl and naphthyl. A variety of photographic tellurium complexes within this formula are useful in the photographic element. The selection of an optimum tellurium complex within the formula will depend upon such factors as the desired degree of photosensitivity, processing conditions, desired image, other components of the photographic material and the like. Especially useful tellurium complexes are those wherein R' is phenyl, M is lead, tin or germanium and R is alkyl as described. Especially useful tellurium complexes are those selected from the group consisting of $C_6H_5TePb(C_6H_5)_3$, $C_6H_5TeGe(C_6H_5)_3$, $C_6H_5TeSn(C_6H_5)_3$, and combinations thereof.

The term "complex" as used herein is intended to include any type of bonding or complexing mechanism which enables the resulting material to have the desired properties for imaging, for example, which enables the resulting material to provide oxidizing properties and the described oxidation-reduction image-forming combination in a heat-developable material. In some instances, the exact bonding of the described tellurium complexes is not fully understood. Accordingly, the term "complex" is intended to include salts and compounds and like forms of bonding.

Certain complexes within the described formula wherein M is lead, tin, germanium or silicon and R and R' are each aryl containing 6 to 12 carbon atoms can be prepared by new processes. These complexes and complexes wherein R and R' are alkyl or aryl can be prepared by a simplified method according to the invention. This method of preparing the described complexes comprises the steps, in sequence, of (a) reacting a diaryl or dialkyl telluride containing up to 12 carbon atoms, with a reducing agent and an alkali metal hydroxide to provide an alkali metal salt of the telluride, and then (b) reacting the resulting alkali metal salt from (a) with a compound represented by the formula: M(R')$_3$Cl, wherein M is as described, to provide the desired Te(II) complex. An advantage of this process is that it enables the elimination of several steps in the preparation, i.e., if desired steps (a) and (b) can be carried out without separating the product from (a).

A representative example of this method of preparation is the preparation of a Te(II) complex represented by the formula: $(C_6H_5)TeGe(C_6H_5)_3$ comprising the steps, in sequence, of (a) reacting diphenyl ditelluride with sodium borohydride in a sodium hydroxide solution to provide the sodium salt of the telluride, and then (b) reacting the resulting sodium salt from (a) with a compound represented by the formula: $(C_6H_5)_3GeCl$ to provide the desired Te(II) complex.

The temperature and pressure condition ranges for the described process will depend upon such factors as the particular reactants, the desired end use, desired reaction rate, reactant concentrations, and the like. Typically, the process is carried out at a temperature within the range of about 50° C. to about 100° C. at atmospheric pressure. In some instances, it may be necessary to use temperatures and pressure outside these ranges to achieve optimum results.

In some instances in preparation of complexes and materials within the scope of the invention which are photosensitive, it can be desirable to carry out the preparation under dark conditions to avoid premature light exposure. However, not all of the complexes within the described formulas are photosensitive to a degree which would adversely affect their preparation under conventional room light conditions.

The reactants are typically admixed in about stoichiometric ratios. However, it can be desirable to admix one of the reactants in excess, such as up to about a ten-fold excess, to provide more desirable reaction rate. A solvent can also be used with the reactants if desired. Typical solvents include, for instance, benzene, ethanol, toluene and methanol. The reactants are typically mixed in more concentrated form, however, to facilitate reaction of the sodium salt with the germanium, tin, lead or silicon compound and to help prevent reformation of the telluride reactant.

A reducing agent such as sodium borohydride can be used in the described reaction to aid the process. Other useful reducing agents can be useful in place of the sodium borohydride if desired. These include, for instance, amine boranes, such as dimethyl amine borane, and other borane type reducing agents which are sufficiently active, such as tetrahydrofuran borane, hydrazine and substituted hydrazines as well as sodium hypophosphite.

While sodium hydroxide is an especially useful base for the described preparation, other strong bases can be useful if desired. These include, for instance, other strong alkali metal hydroxides, for instance, potassium hydroxide and lithium hydroxide.

The metal halide compound useful in the described process can be a chloride, bromide or iodide. The chloride is especially useful. The halide can be replaced with a suitable carboxylate such as an acetate or trifluoroacetate moiety if desired.

The tellurium complexes within the described formula that are considered to be sufficiently photosensitive to be useful as a photosensitive component in an imaging material are those which require energy at or below about $10^7$ to about $10^8$ ergs per square centimeter to provide a developed maximum image density of 1.0. While other tellurium complexes within the described formulas may have a degree of photosensitivity, if the complex does not have the degree of photosensitivity within the described range, it is not considered to be especially useful for purposes of imaging in which the tellurium complex is used as the photosensitive component. The tellurium complexes within the described formula which have less than this degree of photosensitivity are useful as oxidizing agents in the described heat-developable photographic materials and for other purposes. An important advantage for the described tellurium complexes is that photosensitive materials in which they are useful do not require that the image provided be subsequently stabilized by a separate stabilizing step or stabilizer or stabilizer precursor to prevent post-processing deterioration of the developed image. This advantage helps reduce the cost of imaging materials in which the described tellurium materials are useful.

It can be useful to provide a photographic material according to the invention containing a combination of (a) the described tellurium complex according to the invention with (b) a photosensitive component, such as a photosensitive metal salt or complex which can provide the desired developable nuclei upon imagewise exposure in those cases where the tellurium complex is not adequate for this purpose. The photosensitive component can be any photosensitive metal salt or complex which provides the desired developable nuclei upon imagewise exposure. An especially useful photosensitive metal salt comprises silver halide due to its high degree of photosensitivity. A typical concentration of photosensitive metal salt, such as photosensitive silver halide, is from about 0.0001 to about 10.0 moles of the photosensitive metal salt per mole of tellurium complex in the photographic material. For instance, a typical photographic material can contain a concentration of photosensitive silver halide that is within the range of about 0.001 to about 2.0 moles of photosensitive silver halide per mole of the described tellurium complex. Other photosensitive materials which can be useful with the described tellurium complexes include silver dye complexes such as those described in U.S. Pat. No. 3,647,439 of Bass, issued Mar. 7, 1972. Preferred photosensitive silver halides are silver chloride, silver bromide, silver bromoiodide, silver chlorobromoiodide or mixtures thereof. For purposes of the invention, silver iodide is also considered to be a useful photosensitive silver halide. Very fine grained photographic silver halide is especially useful although coarse or fine grained photographic silver halide can be employed if desired. The photographic silver halide can be prepared by any of the procedures known in the photographic art. Such procedures and forms of photographic silver halide are described, for example, in the *Product Licensing Index*, Volume 92, December 1971, publication 9232, on page 107, paragraph I, published by Industrial Opportunities Ltd., Homewell, Havant, Hampshire, PO9 1EF, UK. The photographic silver halide as described can be unwashed or washed, can be chemically sensitized using chemical sensitization procedures known in the art, can be protected against the production of fog and stabilized against loss of sensitivity during keeping as described in the above *Product Licensing Index* publication on pages 107–110.

The photosensitive materials according to the invention can incorporate a variety of reducing agents. These reducing agents can be organic reducing agents or inorganic reducing agents. Reducing agents which are especially useful are typically silver halide developing agents. Examples of useful organic reducing agents include polyhydroxy benzenes, such as hydroquinone, alkyl-substituted hydroquinones, including tertiary butylhydroquinone, isopropylhydroquinone, methylhydroquinone, 2,5-dimethylhydroquinone and 2,6-dimethylhydroquinone; catechols and pyrogallols; chloro-substituted hydroquinones, such as chlorohydroquinone or dichlorohydroquinone; alkoxy-substituted hydroquinones, such as methoxyhydroquinone or ethoxyhydroquinone; aminophenol reducing agents such as 2,4-diaminophenols and methylaminophenols; ascorbic acid reducing agents, such as ascorbic acid, ascorbic acid ketals and ascorbic acid derivatives; hydroxylamine reducing agents; 3-pyrazolidone reducing agents, such as 1-phenyl-3-pyrazolidone and 4-methyl-4-hydroxymethyl-1-phenyl-3-pyrazolidone; reductone reducing agents, such as 2-hydroxy-5-methyl-3-piperidino-2-cyclopentanone; sulfonamidophenol reducing agents such as the sulfonamidophenol reducing agents described in U.S. Pat. No. 3,801,321 of Evans et al, issued Apr. 2, 1974; and the like. Useful inorganic reducing agents include those described in, for example, U.S. Pat. No. 3,598,587 of Yudelson et al, issued Aug. 10, 1971. Combinations of reducing agents can be useful if desired. Selection of an optimum reducing agent or reducing agent combination will depend upon such factors such as processing conditions, desired image, particular tellurium complex, other components of the imaging material and the like.

An especially useful embodiment of the invention comprises a photothermographic element or composition comprising, in reactive association: (a) a photosensitive metal salt, as described, such as photosensitive silver halide, (b) an image-forming combination comprising: (i) a Te(II) complex represented by the formula: $RTeM(R')_3$ wherein M is lead, tin, germanium or silicon; R and R' are each selected from the group consisting of alkyl containing 1 to 12 carbon atoms and aryl containing 6 to 12 carbon atoms, also as described, with (ii) a reducing agent, typically a silver halide developing agent and (c) a binder. The photosensitive metal salt in the photothermographic material is typically a photosensitive silver salt, such as photosensitive silver halide, as described. The reducing agent is typically a silver halide developing agent as described. Combinations of reducing agents can be especially useful in this embodiment. Organic reducing agents are preferred, typically those selected from the group consisting of sulfonamidophenol, ascorbic acid, 3-pyrazolidone, hydroquinone, reductone and aminophenol reducing agents. Inorganic reducing agents, such as those described, for example, in U.S. Pat. No. 3,598,587 of Yudelson et al, issued Aug. 10, 1971, can be useful in this embodiment also.

The described photothermographic materials according to the invention can comprise other oxidizing agents than the described tellurium complex oxidizing agents if desired. For example, the photothermographic materials can contain a silver salt oxidizing agent, such as a silver salt of a long-chained fatty acid. Such silver salt oxidizing agents are typically resistant to darkening upon illumination. Useful silver salts of long-chained fatty acids are those containing about 17 to about 30 carbon atoms. Compounds which are useful silver salt oxidizing agents include, for instance, silver behenate, silver stearate, silver oleate, silver laurate, silver hydroxy stearate, silver caprate, silver myristate, and silver palmitate. Silver salts which are not silver salts of long-chain fatty acids can be useful in combination with the described tellurium complexes also. Such silver salt oxidizing agents include, for instance, silver benzotriazole, silver benzoate, silver terephthalate, silver complexes of certain heterocyclic moieties and the like. Combinations of oxidizing agents can be useful. Examples of other metal oxidizing agents which can be useful are gold stearate, mercury behenate and gold behenate. Selection of an optimum oxidizing agent or oxidizing agent combination will depend upon such factors as the desired image, processing conditions, particular photosensitive component, particular Te(II) complex and the like.

The Te(II) complexes according to the invention can be useful in a photosensitive material in combination with a tellurium complex as described in copending U.S. Application Ser. No. 703,477 of Lelental and Gysling, filed July 8, 1976, now abandoned, the disclosure of which is incorporated herein by reference.

An especially useful photothermographic material according to the invention is a photothermographic element comprising a support having thereon, in reactive association, (a) photosensitive silver halide, (b) an image-forming combination comprising (i) $C_6H_5TeGe(C_6H_5)_3$, with (ii) a sulfonamidophenol or 3-pyrazolidone silver halide developing agent, as described, and (c) a polymeric binder.

Another embodiment of the invention is a non-silver photothermographic material comprising a photosensitive metal compound which is not a silver compound. This embodiment comprises a photothermographic element or composition comprising, in reactive association, (a) a photosensitive metal compound selected from the group consisting of photosensitive copper, tellurium and palladium compounds and combinations thereof, with (b) an image-forming combination comprising (i) a Te(II) complex, as described, with (ii) an organic reducing agent, also as described, and (c) a polymeric binder.

The selection of an optimum concentration of each of the described components of a photosensitive element or composition according to the invention will depend upon such factors as the desired image, particular tellurium complex, processing conditions, other components of the photosensitive material and the like. A range of concentration of reducing agent is useful in the described photosensitive materials according to the invention. Typically, a useful concentration of reducing agent is within the range of about 0.1 to about 100 moles of reducing agent per mole of the described oxidizing agent in the photothermographic element or composition according to the invention. A preferred concentration of reducing agent is within the range of about 0.5 to about 10 moles of reducing agent per mole of the described oxidizing agent, such as per mole of described Te(II) complex. Typically, the concentration of reducing agent in a photothermographic element is within the range of about 0.1 to about 1000 milligrams of reducing agent per square foot of support which corresponds to about 0.01 to about 100 milligrams per square decimeter. An especially useful concentration of the described reducing agent is within the range of about 1 to about 500 milligrams of reducing agent per square foot which corresponds to about 0.1 to about 50 milligrams of reducing agent per square decimeter.

The selection of an optimum concentration of tellurium complex will depend upon such factors as the particular function of the tellurium complex in the photosensitive or imaging material, the particular tellurium complex, the desired image, processing conditions, and the like. Certain of the described Te(II) complexes have a sufficient degree of photosensitivity to be useful as the only photosensitive component in a photosensitive element or composition according to the invention. When a photosensitive tellurium complex is used in combination with another photosensitive component, typically the ratio of the described Te(II) complex to the other photosensitive component will depend upon the described factors. The total concentration of photosensitive components in a photosensitive element or composition according to the invention will also depend upon the described factors. The Te(II) complex can function as both a photosensitive component, such as in combination with photosensitive silver halide or with a different non-silver photosensitive metal salt, and an oxidizing agent in an image-forming combination according to the invention. If the Te(II) complex serves this dual function or other functions in a photosensitive material according to the invention, the concentration of Te(II) complex can be adjusted accordingly. An especially useful concentration of the described tellurium complex when it is used as a photosensitive component in a photosensitive element is a concentration within the range of about 30 to about 150 mg. per square foot of support which corresponds to a concentration within the range of about 320 to about 1620 mg. per square meter of support. When the described tellurium complex is used as an oxidizing agent in an image-forming combination in a photothermographic element as described, a useful concentration of Te(II) complex as described is within the range of about 30 to about 150 mg. of Te(II) complex per square foot of support which corresponds to about 320 to about 1620 per square meter of support.

While a stabilizer or stabilizer precursor is not necessary in most cases in which the tellurium complex is employed as the sole photosensitive component in a photosensitive material according to the invention, it is often desirable to employ a stabilizer or a stabilizer precursor in the described photosensitive material in those instances in which a high degree of post-processing stability is desired. In some cases the tellurium complexes are sufficiently stable after processing. In the case of photosensitive materials according to the invention that contain a photosensitive silver salt, such as photosensitive silver halide, it can be desired to stabilize the photosensitive silver salt after processing in order to avoid undesired post-processing image instability. A variety of stabilizers or stabilizer precursors can be useful in the photothermographic materials as described. These stabilizers or stabilizer precursors can be useful alone or in combination. Typically useful stabilizers or stabilizer precursors include photolytically activated polybrominated organic compounds, such as described in U.S. Pat. No. 3,874,946 of Costa et al, issued Apr. 1, 1975 and sulfur-containing compounds which form a stable silver mercaptide upon heating, such as described in Belgian Pat. No. 768,071 issued July 30, 1971 and the like.

A range of concentration of stabilizer or stabilizer precursor can be useful in the described photothermographic materials. An optimum concentration of stabilizer or stabilizer precursor will depend upon such factors as the particular Te(II) complex, processing conditions, desired stability of image, particular photographic component, and the like. A typical concentration of stabilizer or stabilizer precursor is within the range of about 0.001 to about 100 moles of stabilizer or stabilizer precursor per mole of photosensitive component, such as photosensitive silver salt in the photothermographic material. Preferably a concentration of stabilizer or stabilizer precursor is within the range of about 0.01 to about 10 moles of stabilizer or stabilizer precursor per mole of photosensitive component, such as photosensitive silver halide.

The elements and compositions according to the invention, especially the photothermographic elements and compositions, can contain various colloids and polymers alone or in combination as vehicles, binding agents and in various layers. Suitable materials can be hydrophobic or hydrophilic. They are transparent or translucent and include both naturally occurring substances such as proteins, for example, gelatin, gelatin derivatives, cellulose derivatives, polysaccharides, such as dextran, gum arabic and the like; and synthetic polymeric substances such as water soluble polyvinyl compounds like poly(vinylpyrrolidone), acrylamide polymers and the like. Synthetic polymeric compounds which can be useful include dispersed vinyl compounds, such as in latex form, and particularly those which increase dimensional stability of photographic materials. Effective polymers include water insoluble polymers such as polymers of alkylacrylates and methacrylates, acrylic acid, sulfoalkylacrylates, and those which have crosslinking sites which facilitate hardening or curing. Especially useful materials are high molecular weight materials and resins which are compatible with the described Te(II) complexes, including poly(vinyl butyral), cellulose acetate butyrate, poly(methylmethacrylate), poly(vinylpyrrolidone), ethyl cellulose, polystyrene, poly(vinyl chloride), polyisobutylene, butadiene-styrene copolymers, vinyl chloride-vinyl acetate copolymers, copolymers of vinyl acetate, vinyl chloride and maleic acid, and poly(vinyl alcohol). Combinations of the described colloids and polymers can also be useful.

In some cases, it can be useful to use an overcoat layer or combination of layers on the described photosensitive element, especially the photothermographic element according to the invention to reduce fingerprinting and abrasion marks and for other purposes. The overcoat layer or layers can be (a) one or more of the described polymers which are also useful as binders or (b) other polymers which are compatible with the photosensitive materials or combinations of these polymers. The polymers useful as overcoat layers for photothermographic materials according to the invention must be able to tolerate the processing temperatures employed. A typical overcoat comprises cellulose acetate, poly(vinyl butyral), gelatin or the like.

The photosensitive material according to the invention can contain a variety of addenda, such as development modifiers that function as speed-increasing compounds, hardeners, plasticizers and lubricants, coating aids, brighteners, spectral sensitizing dyes, absorbing and filter dyes, also as described in the *Product Licensing Index*, Volume 92, December 1971, Publication 9232, pages 107–110, published by Industrial Opportunities Ltd., Homewell, Havant, Hampshire, P09 1EF, UK.

The described elements according to the invention can comprise a variety of supports that can tolerate the processing temperatures employed according to the invention. Typical supports include cellulose ester film, poly(vinylacetal) film, poly(ethylene terephthalate) film, polycarbonate film and polyester film supports as described in U.S. Pat. No. 3,634,089 of Hamb, issued Jan. 11, 1972 and U.S. Pat. No. 3,725,070 of Hamb et al, issued Apr. 3, 1973 and related films and resinous material as well as glass, paper, metal and the like supports which can withstand the processing temperatures employed according to the invention. Typically a flexible support is most useful.

The photosensitive materials according to the invention can be coated on a suitable support by various coating procedures known in the photographic art including dip coating, air knife coating, curtain coating or extrusion coating using hoppers such as described in U.S. Pat. No. 2,681,294 of Beguin, issued June 15, 1954. If desired, two or more layers can be coated simultaneously as known in the photographic art.

Spectral sensitizing dyes can be useful in the described elements and compositions of the invention to confer additional sensitivity to the elements and compositions. Useful sensitizing dyes are described, for example, in the *Product Licensing Index,* Volume 92, December 1971, Publication 9232, pages 107–110, paragraph XV, published by Industrial Opportunities Ltd., Homewell, Havant, Hampshire, P09 1EF, UK.

The described components of the photosensitive materials according to the invention can be in any suitable location in the described elements according to the invention which provides the desired image. If desired, one or more of the components of the described element can be in one or more layers of the element. For example, in some cases it can be desirable to include certain percentages of the described reducing agents, image stabilizer or stabilizer precursors and/or other addenda in an overcoat or protective layer on the described element. In some cases this can reduce migration of certain addenda between layers of the described element.

In the elements and compositions of the invention, it is believed that the nuclei formed in the element or composition upon imagewise exposure provide a site for physical development. It is believed that the nuclei, for instance, increase the reaction rate and act as a catalyst for the described image-forming combination containing the tellurium complex and reducing agent. It is believed that, in the case of photothermographic materials, the nuclei enable a lower processing temperature for amplification than otherwise would be possible.

The term "in reactive association" as used herein is intended to mean that the nuclei resulting from imagewise exposure of an element or composition according to the invention are in a location with respect to the other described components, especially the image-forming components, of the material according to the invention which enables this desired lower processing temperature and provides a more useful developed image.

If desired other photosensitive materials, typically heat developable photosensitive materials, can be used in combination with the photosensitive materials according to the invention containing the described tellurium complexes. For instance, a photothermographic element can comprise, in sequence, a support having thereon a photothermographic layer comprising a tellurium complex according to the invention and a separate layer containing a photothermographic material containing photosensitive silver halide as a component with other necessary imaging materials. An example of such a photothermographic element is one containing a heat developable layer (I) contiguous to a Te(II) complex containing heat developable layer (II).

A variety of imagewise exposure means are useful with the photosensitive materials according to the invention. The materials according to the invention are typically sensitive to the ultraviolet and blue regions of the spectrum and exposure means that provide this radiation are preferred. Typically a photosensitive material according to the invention is imagewise exposed to a visible light source, such as a tungsten lamp, although other sources of radiation are useful such as lasers, electron beams, x-ray radiation and the like.

The described photothermographic materials according to the invention can be negative-working or positive-working as desired. The selection of a proper reducing agent can provide a positive-working photothermographic element. An example of a positive-working photothermographic element according to the invention is one which comprises the $(C_6H_5)_3PbTe(C_6H_5)$-$(CH_3)_2NH\cdot BH_3$ redox couple.

An especially useful non-silver photothermographic material, as described, is one comprising in reactive association (a) a photosensitive Te(II) complex, such as disclosed in copending application Ser. No. 703,405 filed July 8, 1976 entitled "Images Formed by Decomposition of Te(II) Coordination Complexes", e.g., [Te(thiourea)$_2$(Cl)$_2$], [Te(1-allyl-2-thiourea)$_2$(Cl)$_2$], [Te(S$_2$COC$_2$H$_5$)$_2$] and [Te(1-(1-naphthyl)-2-thiourea)$_4$]Cl$_2$ with (b) an image-forming combination comprising (i) a Te(II) complex selected from the group consisting of $C_6H_5TePb(C_6H_5)_3$, $C_6H_5TeGe(C_6H_5)_3$, $C_6H_5TeSn(C_6H_5)_3$ and combinations thereof, with (ii) an organic reducing agent, also as described, and (c) a polymeric binder.

A visible image can be developed in a photosensitive material containing a tellurium complex according to the invention by different processing means. A visible image can be developed, for example, in a photothermographic material according to the invention, after imagewise exposure of the material, within a short time merely by overall heating the photothermographic material to a temperature and for a time sufficient to provide development of the image. An image having a maximum reflection density of at least 1.0 and typically at least 1.5 can be provided according to the invention. For example, a photothermographic element according to the invention after imagewise exposure can be heated to a temperature within the range of about 80° C. to about 220° C. until a desired image is developed, typically within about 1 to about 90 seconds. The photothermographic material as described is preferably heated to a temperature within the range of about 100° C. to about 170° C. until the desired image is developed.

Another embodiment of the invention is a process of developing an image in a photothermographic material, as described, comprising overall heating the material to a temperature within the range of about 80° C. to about 220° C. until a desired image is developed.

While photosensitive metal salts can be useful in an element or composition according to the invention, other physically developable metal nuclei are useful for forming images according to the invention. For instance, while photosensitive silver halide is especially useful for producing physically developable metal nuclei according to the invention because of its high degree of photosensitivity, it can be useful in some cases to provide a material according to the invention which is not photosensitive, but rather provides a developable image through other exposure means than exposure to light energy. In those instances, other physically developable nuclei can be useful in elements and compositions according to the invention containing the described Te(II) complex. Other physically developable nuclei which are useful include metal nuclei selected from the group consisting of chromium, iron, cobalt, nickel, copper, cadmium, selenium, palladium, silver, tin, tellurium, osmium, iridium, ruthenium, rhenium, platinum, rhodium, gold and lead nuclei and combinations of these nuclei or metal binary compounds, phosphides, sulfides, oxides, and the like. These nuclei can be provided from any suitable source, such as from compounds which are decomposable through various means to the desired metal nuclei. Such compounds include, for example, $PbCl_2$, $K_3Co(C_2O_4)_3$, $[Co(NH_3)_5N_3]Cl_2$, and $Se(S_2COi\text{-}C_3H_7)_2$. Certain combinations of these can also be useful.

Especially useful physically developable metal nuclei are selected from the group consisting of tellurium, palladium, copper and silver nuclei. These metal nuclei can be formed from photographic or non-photographic tellurium, palladium, copper and/or silver compounds. Examples of such compounds include: $Te(S_2P(OCH_3)_2)_2$, $K_2Pd(C_2O_4)_2$, $Pd(P(C_6H_5)_3)_2(C_2O_4)$, $[Cu(P(OCH_3)_3)_4]B(C_6H_5)_4$, $[Cu(P(OCH_3)_3)_3BH_3CN]_2$, $Cu(Sb(C_6H_5)_3)_3Cl$, and $[Cu(ethylenediamine)_2][B(C_6H_5)_4]_2$. Certain combinations of these can also be useful. Other photosensitive palladium complexes which are useful for forming developable nuclei are described in, for example, U.S. Pat. No. 3,719,490 of Yudelson and Gysling, issued Mar. 6, 1973 and Research Disclosure, September 1975, No. 13705 of B. F. Nellis. Useful copper complexes for forming developable nuclei are described, for example, in U.S. Pat. No. 3,859,092 of Gysling and Vinal, issued Jan. 7, 1975; U.S. Pat. No. 3,860,500; U.S. Pat. No. 3,860,501; U.S. Pat. No. 3,927,055; and U.S. Pat. No. 3,880,724 of Gysling.

A useful embodiment according to the invention is a heat developable imaging material comprising, in reactive association, (a) physically developable metal nuclei selected from the group consisting of titanium, vanadium, chromium, iron, cobalt, nickel, copper, zinc, germanium, cadmium, selenium, palladium, silver, tin, tellurium, osmium, iridium, rhenium, ruthenium, platinum, gold and lead nuclei and combinations of these nuclei, with (b) an image-forming combination comprising (i) a Te(II) complex, as described, and (ii) a reducing agent, also as described, and (c) a binder.

Especially useful materials within this embodiment comprise in reactive association (a) physically developable metal nuclei selected from the group consisting of tellurium, palladium, copper and silver nuclei and combinations of these nuclei, with (b) an image-forming combination comprising (i) a Te(II) complex, as described, and (ii) an organic reducing agent selected from the group consisting of sulfonamidophenol, ascorbic acid, 3-pyrazolidone, hydroquinone, reductone and aminophenol reducing agents, and combinations thereof, and (c) a polymeric binder.

Development of an image in a photosensitive material according to the invention can be provided with a diffusion transfer process. In one embodiment of such a process a photosensitive element comprising a photosensitive metal salt, for example, a photosensitive salt of silver, palladium, tellurium or copper, is imagewise exposed to provide a developable latent image and is then contacted with a receiving sheet containing an image-forming combination comprising a Te(II) complex, as described, and a reducing agent according to the invention. When the element and receiving sheet are in contact, heat is applied to provide diffusion of unexposed photosensitive metal salt from the photosensitive element to the receiving sheet. Heating the so-called sandwich to a temperature within the range of about 45° to about 200° C. is useful. In the unexposed areas of the photosensitive element, the metal salt migrates from the element to the receiving sheet where it is reduced and catalyzes the reduction of the tellurium complex to tellurium metal in the sheet to form a positive image in the receiving sheet.

In another embodiment of a diffusion transfer process, the photosensitive element comprises at least one photosensitive layer having permanently associated therewith a receiving layer. The photosensitive layer comprises a photosensitive metal salt, as described, and the receiving layer comprises a tellurium composition and a reducing agent according to the invention. This is referred to herein as an integral diffusion transfer material. The photosensitive element is imagewise exposed to provide a developable latent image and is then overall heated to a temperature within the range of about 75° C. to 250° C. to promote the desired diffusion. In the unexposed areas of the photosensitive layer, the metal salt diffuses from the photosensitive layer to the receiving layer where it is reduced and acts as a catalyst as described to form a positive image in the receiving layer.

The following examples are included for a further understanding of the invention.

EXAMPLE 1

Preparation of $(C_6H_5)TeGe(C_6H_5)_3$

Diphenylditelluride (2.56 grams, 0.00625 moles) was dissolved in 3 ml of benzene and 9 ml of ethanol. The resulting mixture was heated to reflux. A solution of sodium borohydride ($NaBH_4$) (0.38 g) in 9 ml of 1 N aqueous sodium hydroxide was added dropwise (the red ditelluride color disappeared as the reduction proceeded). When the addition was complete triphenylgermanium chloride ($(C_6H_5)_3GeCl$)) (5.1 g, 0.015 mol) was added as a solid. The reaction mixture resulting was stirred for 5 minutes and then poured into 50 ml of water and extracted with ether. The ether extract was dried over anhydrous sodium sulfate and reduced to dryness. The resulting desired product was recrystallized from hexane providing 3.9 g (61%) of a light yellow solid having a melting point of 105°–107° C. Elemental and other analyses indicated the preparation of the desired $(C_6H_5)TeGe(C_6H_5)_3$.

EXAMPLE 2

Preparation of $(C_6H_5)TeSn(C_6H_5)_3$

The procedure described in Example 1 was repeated except that 5.78 g (0.015 mol) of triphenyltin chloride ($(C_6H_5)_3SnCl$)) was substituted for the triphenylgermanium chloride and the reaction mixture was extracted with two 275 ml portions of ether. The resulting desired product was light yellow in color and had a melting point of 95°–97° C. 5.3 g of the desired product was produced (76% yield). Elemental and other analyses demonstrated preparation of the desired $(C_6H_5)TeSn(C_6H_5)_3$.

EXAMPLE 3

Preparation of $C_6H_5TePb(C_6H_5)_3$

The procedure described in Example 1 was repeated except that 7.11 g (0.015 mol) of triphenyllead chloride (($C_6H_5)_3PbCl$)) was used in place of the described triphenylgermanium chloride and the reaction mixture was extracted with two 100 ml portions of ether. The desired product was light yellow in color and it had a melting point of 90°–92° C. 6.0 g of the desired product (75% yield) was prepared. Elemental and other analyses demonstrated preparation of the desired $C_6H_5TePb(C_6H_5)_3$.

EXAMPLES 4–10

Preparation of other Te(II) Complexes

The procedure described in Example 1 was repeated with the exception that the described chloride was replaced with an appropriate chloride for preparation of the tellurium complex described in the column designated "Formula" in the following Table 1 and the reaction mixture was extracted with an appropriate portion of ether. The results of these preparations including the melting point and yield of the desired product are given in the following Table 1:

Table 1

Compounds of Formula $ArTeM\phi_3$ (Ar = Aryl; M = Ge, Sn or Pb; $\phi$ = phenyl)

| Example No. | Formula | MP(°C.) | Yield (%) |
|---|---|---|---|
| 4 | p-$CH_3C_6H_4TeGe\phi_3$ | 88–90 | 60 |
| 5 | p-$CH_3OC_6H_4TeGe\phi_3$ | 89–91 | 23 |
| 6 | p-$CH_3C_6H_4TeSn\phi_3$ | 78–80 | 61 |
| 7 | p-$CH_3OC_6H_4TeSn\phi_3$ | 78–80 | 65 |
| 8 | p-$CH_3C_6H_4TePb\phi_3$ | 87–9 | 67 |
| 9 | p-$CH_3OC_6H_4TePb\phi_3$ | 71–3 | 60 |
| 10 | p-$BrC_6H_4TePb\phi_3$ | 80–2 | 64 |

The reactions described in Examples 1 through 10 can be carried out under the described conditions with up to about 10 fold more dilution with a suitable solvent; however, more concentrated conditions are preferred to facilitate the reaction and prevent reformation of the starting telluride.

EXAMPLE 11

Material containing Te(II) complex according to the invention

An element was prepared by the following steps: 100 mg of $(C_6H_5)_3GeTeC_6H_5$ and 100 mg of dimethylamine borane (reducing agent) were dissolved in 10 ml of a 4% by weight solution of poly(vinyl formal) in chloroform. The resulting solution was then coated at an 8 mil wet coating thickness on a poly(ethylene terephthalate) film support. A piece of the resulting film was then laminated at 150° C. with a step tablet distribution of palladium nuclei vacuum deposited on a poly(ethylene terephthalate) film support. The step tablet distribution contained six density steps with each successive step decreasing by ½ in coverage. The highest coverage of palladium nuclei consisted of 0.8 mg of palladium per square foot which is equivalent to 8.6 mg per square meter. A developed, gray negative image was produced in the material at 0.4 mg of palladium per square foot.

Each of the tellurium complexes of Examples 2, 4, 5, 6 and 7 were incorporated in individual elements prepared according to the above procedure. In each instance, the film containing the layer comprising the Te(II) complex and the reducing agent was laminated to the described palladium nuclei vacuum deposited layer on the described film support. The resulting laminate was heated at 150° C. to provide a developed, gray negative image at 0.4 mg of palladium per square foot. The image was visible to 0.2 mg of palladium per square foot.

EXAMPLE 12

Positive working material according to the invention

A tellurium complex which was $(C_6H_5)_3PbTeC_6H_5$ (100 mg) and dimethylamine borane (100 mg) were dissolved in 10 ml of a 4% by weight solution of poly(vinyl formal) in chloroform. The resulting solution was coated at an 8 mil wet coating thickness of a poly(ethylene terephthalate) film support. Strips of the resulting film were laminated at 150° C. with a step tablet distribution of palladium nuclei on poly(ethylene terephthalate) film support (prepared as described in Example 11). This resulted in a black, developed positive image with undeveloped areas visible to 0.1 mg of palladium per square foot.

Each of the tellurium complexes described in Examples 8, 9 and 10 in Table 1 were incorporated in the same manner to provide an element. In each instance, a developed, brown positive image was provided with clear areas visible to at least 0.2 mg per square foot of palladium.

EXAMPLE 13

Photosensitive material according to the invention

A tellurium complex which was $(C_6H_5)_3GeTeC_6H_4$-p-$CH_3$ (50 mg) was dissolved in 50 ml of chloroform. The resulting solution was imbibed into a paper support. Strips of the resulting paper were exposed imagewise for 5 minutes to a mercury arc light source at a distance of 12 inches to provide a developable latent image. The resulting exposed paper was then heated overall by contacting it with a metal block at 120°–150° C. for 15 seconds. A brown negative image was developed having a maximum density of 1 and a minimum density of 0.1.

The invention has been described in detail with particular reference to certain preferred embodiments thereof, but it will be understood that variations and modifications can be effected within the spirit and scope of the invention.

What is claimed is:

1. A photothermographic element comprising a support having thereon in binder, in reactive association:
    (a) a photosensitive metal salt, and
    (b) an image-forming combination comprising:
        (i) a Te(II) complex represented by the formula: $RTeM(R')_3$ wherein M is Pb, Sn, Ge or Si; R and R' are each selected from the group consisting of alkyl containing 1 to 12 carbon atoms and aryl containing 6 to 12 carbon atoms, with
        (ii) a reducing agent for said complex.

2. A photothermographic element as in claim 1 wherein said photosensitive metal salt is a photosensitive silver salt.

3. A photothermographic element as in claim 1 wherein said photosensitive silver salt is photosensitive silver halide.

4. A photothermographic element as in claim 1 wherein said Te(II) complex is represented by the formula:

RTePb(phenyl)$_3$ wherein R is alkyl containing 1 to 12 carbon atoms or aryl containing 6 to 12 carbon atoms.

5. A photothermographic element as in claim 1 wherein said Te(II) complex is represented by the formula:

RTeSn(phenyl)$_3$ wherein R is alkyl containing 1 to 12 carbon atoms or aryl containing 6 to 12 carbon atoms.

6. A photothermographic element as in claim 1 wherein said Te(II) complex is represented by the formula:

RTeGe(phenyl)$_3$ wherein R is alkyl containing 1 to 12 carbon atoms or aryl containing 6 to 12 carbon atoms.

7. A photothermographic element as in claim 1 wherein said reducing agent is a silver halide developing agent.

8. A photothermographic element as in claim 1 wherein said reducing agent is a sulfonamidophenol silver halide developing agent.

9. A photothermographic element as in claim 1 wherein said binder is a poly(vinyl formal) or poly(vinylbutyral) binder.

10. A photothermographic element as in claim 1 wherein said Te(II) complex is selected from the group consisting of
C$_6$H$_5$TePb(C$_6$H$_5$)$_3$,
C$_6$H$_5$TeGe(C$_6$H$_5$)$_3$,
C$_6$H$_5$TeSn(C$_6$H$_5$)$_3$, and
combinations thereof.

11. A photothermographic element comprising a support having thereon, in a polymeric binder, in reactive association,
(a) photosensitive silver halide, and
(b) an image-forming combination comprising
  (i) C$_6$H$_5$TeGe(C$_6$H$_5$)$_3$, with
  (ii) a sulfonamidophenol or 3-pyrazolidone silver halide developing agent.

12. A photothermographic element comprising a support having thereon, in a polymeric binder, in reactive association,
(a) a photosensitive metal compound selected from the group consisting of photosensitive copper, tellurium and palladium compounds and combinations thereof, and
(b) an image-forming combination comprising
  (i) a Te(II) complex represented by the formula:

RTeM(R')$_3$ wherein M is Pb, Sn, Ge or Si; R and R' are each selected from the group consisting of alkyl containing 1 to 12 carbon atoms and aryl containing 6 to 12 carbon atoms, with
  (ii) an organic reducing agent for said complex.

13. A photothermographic element as in claim 12 that is a positive-working element.

14. A photothermographic element comprising a support having thereon, in a polymeric binder, in reactive association,
(a) a photosensitive tellurium compound, with
(b) an image-forming combination comprising
  (i) a Te(II) complex selected from the group consisting of
  C$_6$H$_5$TePb(C$_6$H$_5$)$_3$,
  C$_6$H$_5$TeGe(C$_6$H$_5$)$_3$,
  C$_6$H$_5$TeSn(C$_6$H$_5$)$_3$ and
  combinations thereof, with
  (ii) an organic reducing agent for said complex.

15. A heat developable, imaging element comprising a support having thereon, in a binder, in reactive association,
(a) physically developable metal nuclei selected from the group consisting of titanium, vanadium, chromium, iron, cobalt, nickel, copper, zinc, germanium, cadmium, selenium, palladium, silver, tin, tellurium, osmium, iridium, ruthenium, rhenium, platinum, gold and lead nuclei and combinations of said nuclei,
(b) an oxidation-reduction image-forming combination comprising
  (i) a Te(II) complex represented by the formula:

RTeM(R')$_3$ wherein M is Pb, Sn, Ge or Si; R and R' are each selected from the group consisting of alkyl containing 1 to 12 carbon atoms and aryl containing 6 to 12 carbon atoms, with
  (ii) a reducing agent for said complex.

16. A heat developable, imaging element comprising a support having thereon, in a polymeric binder, in reactive association,
(a) physically developable metal nuclei selected from the group consisting of tellurium, palladium, copper and silver nuclei and combinations of said nuclei, and
(b) an image-forming combination comprising
  (i) a Te(II) complex represented by the formula:

RTeM(phenyl)$_3$ wherein M is Pb, Sn, Ge or Si; R is alkyl containing 1 to 12 carbon atoms or aryl containing 6 to 12 carbon atoms, with
  (ii) an organic reducing agent selected from group consisting of sulfonamidophenol, ascorbic acid, 3-pyrazolidone, hydroquinone, reductone and aminophenol reducing agents and combinations thereof for said complex.

17. A heat developable, imaging element as in claim 15 wherein said Te(II) complex is a complex selected from the group consisting of
C$_6$H$_5$TePb(C$_6$H$_5$)$_3$,
C$_6$H$_5$TeGe(C$_6$H$_5$)$_3$,
C$_6$H$_5$TeSn(C$_6$H$_5$)$_3$, and combinations thereof.

18. A photographic composition comprising a photosensitive metal salt and
  (i) a photosensitive Te(II) complex represented by the formula:

RTeM(R')$_3$ wherein M is Pb, Sn, Ge or Si; R and R' are each selected from the group consisting of alkyl containing 1 to 12 carbon atoms and aryl containing 6 to 12 carbon atoms, with
(ii) a reducing agent for said complex.

19. A photographic composition as in claim 18 also comprising a binder.

20. A photographic composition as in claim 18 also comprising a polymeric binder.

21. A photographic composition as in claim 18 also comprising a photosensitive silver salt.

22. A photographic composition as in claim 18 also comprising photosensitive silver halide.

23. A photographic composition as in claim 18 also comprising a silver halide developing agent.

24. A photographic composition as in claim 18 wherein said Te(II) complex is represented by the formula:

$$RTeM(phenyl)_3$$

wherein M is Pb, Sn, Ge or Si; R is alkyl containing 1 to 12 carbon atoms or aryl containing 6 to 12 carbon atoms.

25. A photographic composition as in claim 18 wherein said Te(II) complex is selected from the group consisting of
$C_6H_5TePb(C_6H_5)_3$,
$C_6H_5TeGe(C_6H_5)_3$,
$C_6H_5TeSn(C_6H_5)_3$ and combinations thereof.

26. A photographic composition comprising a photosensitive metal salt and
(i) $C_6H_5TePb(C_6H_5)_3$, with
(ii) a 3-pyrazolidone developing agent, and a polymeric binder.

27. A photographic composition comprising a photosensitive metal salt and
(i) $C_6H_5TeSn(C_6H_5)_3$ with
(ii) a 3-pyrazolidone developing agent, and a polymeric binder.

28. A photographic composition comprising a photosensitive metal salt and
(i) $C_6H_5TeGe(C_6H_5)_3$ with
(ii) a 3-pyrazolidone developing agent, and a polymeric binder.

29. A photothermographic composition comprising
(a) a photosensitive metal salt,
(b) an image-forming combination comprising:
(i) a Te(II) complex represented by the formula:

$$RTeM(R')_3$$

wherein M is Pb, Sn, Ge or Si; R and R' are each selected from the group consisting of alkyl containing 1 to 12 carbon atoms and aryl containing 6 to 12 carbon atoms, with
(ii) a reducing agent, and
(c) a binder.

30. A photothermographic composition as in claim 29 wherein said photosensitive metal salt is a photosensitive silver salt.

31. A photothermographic composition as in claim 29 wherein said photosensitive metal salt is a photosensitive silver halide.

32. A photothermographic composition as in claim 29 wherein said Te(II) complex is represented by the formula:

$$RTeM(phenyl)_3$$

wherein M is Pb, Ge or Sn; and R is alkyl containing 1 to 12 carbon atoms or aryl containing 6 to 12 carbon atoms.

33. A photothermographic composition as in claim 29 wherein said reducing agent is a silver halide developing agent.

34. A photothermographic composition as in claim 29 wherein said reducing agent is a sulfonamidophenol silver halide developing agent.

35. A photothermographic composition as in claim 29 wherein said binder is a poly(vinyl formal) or poly(vinyl butyral) binder.

36. A photothermographic composition as in claim 29 wherein said Te(II) complex is selected from the group consisting of
$C_6H_5TePb(C_6H_5)_3$,
$C_6H_5TeGe(C_6H_5)_3$,
$C_6H_5TeSn(C_6H_5)_3$, and combinations thereof.

37. A photothermographic composition comprising
(a) photosensitive silver halide,
(b) an image-forming combination comprising
(i) $C_6H_5TeGe(C_6H_5)_3$ with
(ii) a sulfonamidophenol or 3-pyrazolidone silver halide developing agent and
(c) a polymeric binder.

38. A photothermographic composition comprising
(a) a photosensitive metal compound selected from the group consisting of photosensitive copper, tellurium and palladium compounds and combinations thereof, with
(b) an image-forming combination comprising
(i) a Te(II) complex represented by the formula:

$$RTeM(R')_3$$

wherein M is Pb, Sn, Ge or Si; R and R' are each selected from the group consisting of alkyl containing 1 to 12 carbon atoms and aryl containing 6 to 12 carbon atoms,
(ii) an organic reducing agent, and
(c) a polymeric binder.

39. A photothermographic composition as in claim 38 that is a positive working composition.

40. A photothermographic composition comprising
(a) a photosensitive tellurium compound, with
(b) an image-forming combination comprising
(i) a Te(II) complex selected from the group consisting of
$C_6H_5TePb(C_6H_5)_3$,
$C_6H_5TeGe(C_6H_5)_3$,
$C_6H_5TeSn(C_6H_5)_3$, and combinations thereof, with
(ii) an organic reducing agent, and
(c) a polymeric binder.

41. A heat developable, imaging composition comprising
(a) physically developable metal nuclei selected from the group consisting of titanium, vanadium, chromium, iron, cobalt, nickel, copper, zinc, germanium, cadmium, selenium, palladium, silver, tin, tellurium, osmium, iridium, ruthenium, rhenium, platinum, gold and lead nuclei, and combinations of said nuclei,
(b) an image-forming combination comprising
(i) a Te(II) complex represented by the formula:

$$RTeM(R')_3$$

wherein M is Pb, Sn, Ge or Si; R and R' are each selected from the group consisting of alkyl containing 1 to 12 carbon atoms and aryl containing 6 to 12 carbon atoms, with
  (ii) a reducing agent, and
(c) a binder.

42. A heat developable, imaging composition comprising
(a) physically developable metal nuclei selected from the group consisting of tellurium, palladium, copper and silver nuclei and combinations of said nuclei,
(b) an image-forming combination comprising
  (i) a Te(II) complex represented by the formula:

RTeM(phenyl)$_3$ wherein M is Pb, Sn, Ge or Si; R is alkyl containing 1 to 12 carbon atoms or aryl containing 6 to 12 carbon atoms, with
  (ii) an organic reducing agent selected from the group consisting of sulfonamidophenol, ascorbic acid, 3-pyrazolidone, hydroquinone, reductone and aminophenol reducing agents, and combinations thereof, and
(c) a polymeric binder.

43. A heat developable, imaging composition as in claim 42 wherein said Te(II) complex is a complex selected from the group consisting of
  $C_6H_5TePb(C_6H_5)_3$,
  $C_6H_5TeGe(C_6H_5)_3$,
  $C_6H_5TeSn(C_6H_5)_3$, and combinations thereof.